(12) United States Patent
Coupard et al.

(10) Patent No.: US 11,492,311 B2
(45) Date of Patent: Nov. 8, 2022

(54) COUPLING OF UNIT FOR EXTRACTING METHYL-SUBSTITUTED AROMATICS WITH UNIT FOR HYDROGENOLYSING ALKYL-AROMATICS

(71) Applicant: IFP Energies nouvelles, Rueil-Malmaison (FR)

(72) Inventors: Vincent Coupard, Rueil-Malmaison (FR); Alexandre Pagot, Rueil-Malmaison (FR); Vanessa Vincent-Genod, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 17/415,040

(22) PCT Filed: Dec. 13, 2019

(86) PCT No.: PCT/EP2019/085013
§ 371 (c)(1),
(2) Date: Jun. 17, 2021

(87) PCT Pub. No.: WO2020/126872
PCT Pub. Date: Jun. 25, 2020

(65) Prior Publication Data
US 2022/0064086 A1    Mar. 3, 2022

(30) Foreign Application Priority Data

Dec. 19, 2018 (FR) ........................ 1873438

(51) Int. Cl.
*C07C 6/12* (2006.01)
*C07C 7/00* (2006.01)
*C07C 7/04* (2006.01)

(52) U.S. Cl.
CPC .............. *C07C 6/126* (2013.01); *C07C 7/005* (2013.01); *C07C 7/04* (2013.01)

(58) Field of Classification Search
CPC ........... C07C 6/126; C07C 7/005; C07C 7/04; C07C 2521/04; C07C 2523/883;
(Continued)

(56) References Cited

U.S. PATENT DOCUMENTS 3,919,339 A * 11/1975 Ransley .................... C07C 4/12
585/481
4,177,219 A * 12/1979 Feinstein ................. B01J 23/60
208/46

(Continued)

FOREIGN PATENT DOCUMENTS

WO        2009008876 A1    1/2009

OTHER PUBLICATIONS

International Search Report for PCT/EP2019/085013 dated Mar. 16, 2020.

(Continued)

*Primary Examiner* — Ali Z Fadhel
(74) *Attorney, Agent, or Firm* — Millen White Zelano & Branigan, PC; Brion P. Heaney

(57) ABSTRACT

The present invention relates to a device and a process for converting aromatic compounds, wherein: methyl-substituted aromatic compounds are extracted from a hydrocarbon feedstock (2) comprising aromatic compounds having at least 8 carbon atoms in an extraction unit (1), to produce at least one effluent enriched in methyl-substituted aromatic compounds (3A, 3B) and an effluent depleted in methyl-substituted aromatic compounds (4); and C2+ alkyl chains of the aromatic compounds of the depleted effluent (4) are converted into methyl groups in a hydrogenolysis unit (5) placed downstream of the extraction unit (1), to produce a
(Continued)

hydrogenolysis effluent enriched in methyl-substituted aromatic compounds (7).

18 Claims, 2 Drawing Sheets

(58) Field of Classification Search
CPC ..... C07C 5/2791; C07C 15/02; C07C 15/073; C07C 15/08; C10G 67/00
See application file for complete search history.

(56) References Cited

U.S. PATENT DOCUMENTS

| | | | | |
|---|---|---|---|---|
| 5,866,741 A | * | 2/1999 | Wu | C07C 6/126 |
| | | | | 585/475 |
| 5,877,374 A | * | 3/1999 | Nacamuli | C07C 5/2737 |
| | | | | 208/138 |
| 5,952,535 A | * | 9/1999 | King | B01J 29/18 |
| | | | | 585/475 |
| 2013/0165727 A1 | * | 6/2013 | Baeck | C07C 5/2775 |
| | | | | 585/488 |
| 2014/0316174 A1 | * | 10/2014 | D'Acosta | C07C 2/66 |
| | | | | 585/475 |
| 2018/0186710 A1 | * | 7/2018 | Abudawoud | C07C 15/24 |

OTHER PUBLICATIONS

English Abstract for WO-2009008876, Publication Date: Jan. 15, 2009.

* cited by examiner

COUPLING OF UNIT FOR EXTRACTING METHYL-SUBSTITUTED AROMATICS WITH UNIT FOR HYDROGENOLYSING ALKYL-AROMATICS

TECHNICAL FIELD

The invention pertains to the conversion of aromatics in the context of the production of aromatics for the petrochemical industry (benzene, toluene, para-xylene, ortho-xylene). The aromatic complex is supplied with C6 to C10+ feedstocks, and the alkyl aromatics are extracted therefrom and then converted into the desired intermediates. The products of interest are aromatics with 0, 1 or 2 methyls, xylenes having the greatest market value. It is therefore advisable to have methyl groups.

PRIOR ART

A hydrodealkylation reaction is a dealkylation reaction (substitution, in a molecule, of a hydrogen atom for an alkyl radical) wherein the removal of the alkyl group from aromatic-type molecules is carried out in the presence of hydrogen. Specifically, it is a terminal cleavage of the alkyl chain "flush" with the ring. The catalysis can be of the acid type, used in particular on alkyl chains with 2 or more carbons but very inefficient for methyls, or of the metal type, when it is desired in particular to convert methyls. The conversion of methyls is used in particular for reducing the cut point of gasolines for which all the molecules must lose carbons, or for the production of benzene for which the reaction is pushed to the maximum in order to keep only the aromatic ring.

A hydrogenolysis reaction is a chemical reaction by which a carbon-carbon or carbon-heteroatom covalent bond is broken down or undergoes lysis by the action of hydrogen. A hydrodealkylation reaction can therefore be considered to be a reaction for hydrogenolysis of the carbon-carbon bond between an alkyl and an aromatic ring. On the other hand, a hydrogenolysis reaction also concerns the carbon-carbon bonds internal to the alkyl group with 2 or more carbons.

Hydrodealkylation units, mainly used to produce high purity benzene from toluene, are known from the prior art. The McDermott (formerly CB&I) LITOL and DETOL processes are examples of hydrodealkylation which can be either thermal or catalytic. Commercial hydrodealkylation units generally use metal catalysis, which involves a reaction of hydrogenolysis type. The term hydrodealkylation is therefore not exclusive and alkyls with 2 or more carbons also undergo hydrogenolysis therein. Units of this type can be called alkyl aromatic hydrogenolysis units.

The units mentioned above are used either to produce benzene from heavier mono-aromatics (toluene, xylenes, etc.), or to reduce the cut point of gasolines. No particular attention is paid to the total amount of methyls available after the conversion unit.

Application FR 17 56905 relates to a selective hydrogenolysis unit that treats a feedstock rich in aromatic compounds having more than 8 carbon atoms, and that consists in converting one or more alkyl group(s) having at least two carbon atoms (ethyl, propyl, butyl, isopropyl, etc.) attached to a benzene ring into one or more methyl group(s).

SUMMARY OF THE INVENTION

In the context described above, a first object of the present description is to overcome the problems of the prior art and to provide a process for producing aromatics for the petrochemical industry allowing improved methyl compound selectivity and yield.

According to a first aspect, the aforementioned objects, and also other advantages, are obtained by a device for converting aromatic compounds, comprising:
an extraction unit suitable for extracting methyl-substituted aromatic compounds from a hydrocarbon feedstock comprising aromatic compounds having at least 8 carbon atoms, and producing at least one effluent enriched in methyl-substituted aromatic compounds and one effluent depleted in methyl-substituted aromatic compounds; and
a hydrogenolysis unit placed downstream of the extraction unit and suitable for converting, into methyl groups, C2+ alkyl chains of aromatic compounds of the effluent depleted in methyl-substituted aromatic compounds, and producing a hydrogenolysis effluent enriched in methyl-substituted aromatic compounds.

According to one or more embodiments, the extraction unit is suitable for producing at least one effluent enriched in methyl-substituted aromatic compounds comprising at least 90% by weight of aromatic compounds only substituted with methyls relative to the total weight of said effluent enriched in methyl-substituted aromatic compounds.

According to one or more embodiments, the extraction unit comprises at least one of the following distillation columns:
distillation column suitable for recovering xylenes at the bottom of the column;
distillation column suitable for recovering the methylethylbenzenes at the top of the column;
distillation column suitable for recovering the trimethylbenzenes at the top of the column.

According to one or more embodiments, the extraction unit is suitable for producing at least a second effluent enriched in methyl-substituted aromatic compounds.

According to one or more embodiments, the extraction unit is suitable for:
producing at least one effluent depleted in methyl-substituted aromatic compounds comprising ethylbenzene and at least one effluent enriched in methyl-substituted aromatic compounds comprising meta-xylene and/or ortho-xylene; and/or
producing at least one effluent depleted in methyl-substituted aromatic compounds comprising methylethylbenzenes and/or propylbenzenes and at least one effluent enriched in methyl-substituted aromatic compounds comprising trimethylbenzenes.

According to a second aspect, the abovementioned objects, and also other advantages, are obtained by a device for producing xylenes integrating the device for converting aromatic compounds according to the first aspect, in order to enrich streams in aromatics comprising methyl groups, all or a portion of which are sent to an aromatic complex in order to produce xylenes.

According to one or more embodiments, at least one device for converting aromatic compounds is integrated into an aromatic complex according to at least one of the following configurations:
the at least one device for converting aromatic compounds is used to pretreat the hydrocarbon feedstock upstream of the aromatic complex;
the at least one device for converting aromatic compounds is used to treat at least one cut internal to the aromatic complex.

According to a third aspect, the aforementioned objects, and also other advantages, are obtained by a process for converting aromatic compounds, comprising the following steps:

methyl-substituted aromatic compounds are extracted from a hydrocarbon feedstock comprising aromatic compounds having at least 8 carbon atoms in an extraction unit, in order to produce at least one effluent enriched in methyl-substituted aromatic compounds and one effluent depleted in methyl-substituted aromatic compounds; and C2+ alkyl chains of the aromatic compounds of the effluent depleted in methyl-substituted aromatic compounds are converted into methyl groups in a hydrogenolysis unit placed downstream of the unit for extracting aromatics, in order to produce a hydrogenolysis effluent enriched in methyl-substituted aromatic compounds.

According to one or more embodiments, at least one effluent enriched in methyl-substituted aromatic compounds is produced, comprising at least 90% by weight of aromatic compounds only substituted with methyls relative to the total weight of said effluent enriched in methyl-substituted aromatic compounds.

According to one or more embodiments, at least one of the following compounds is extracted:
xylenes recovered at the bottom of a distillation column,
methylethylbenzenes recovered at the bottom of a distillation column,
trimethylbenzenes recovered at the bottom of a distillation column.

According to one or more embodiments, at least a second effluent enriched in methyl-substituted aromatic compounds is produced.

According to one or more embodiments,
at least one effluent depleted in methyl-substituted aromatic compounds comprising ethylbenzene and at least one effluent enriched in methyl-substituted aromatic compounds comprising meta-xylene and/or ortho-xylene are produced; and/or
at least one effluent depleted in methyl-substituted aromatic compounds comprising methylethylbenzenes and/or propylbenzenes and at least one effluent enriched in methyl-substituted aromatic compounds comprising
trimethylbenzenes are produced.

According to one or more embodiments, the hydrogenolysis unit is used with the following operating conditions:
temperature of between 300° C. and 550° C.;
pressure of between 0.1 and 3 MPa;
$H_2$/HC molar ratio of between 1 and 10;
WWH of between 0.1 and 50 $h^{-1}$.

According to a fourth aspect, the abovementioned objects, and also other advantages, are obtained by a process for producing xylenes integrating the process for converting aromatic compounds according to the third aspect, in order to enrich streams in aromatics comprising methyl groups, all or a portion of which are sent to an aromatic complex in order to produce xylenes.

According to one or more embodiments, the process for converting aromatic compounds is integrated into an aromatic complex according to at least one of the following configurations:
pretreatment of the hydrocarbon feedstock upstream of the aromatic complex;
treatment of at least one cut internal to the aromatic complex.

Embodiments according to the first aspect and the second aspect, and also other features and advantages of the devices and processes according to the abovementioned aspects, will become apparent on reading the description which follows, which is given solely by way of illustration and without limitation, and with reference to the drawings which follow.

DESCRIPTION OF THE EMBODIMENTS

In the petrochemical industry, para-xylene is one of the intermediates with the highest market value. The production thereof requires methyl-substituted monoaromatics; it is mainly produced by toluene disproportionation, isomerization of xylenes or transalkylation of toluene with tri- or tetramethylbenzenes. To maximize the production of para-xylene, it is useful to maximize the amount of methyl group available per aromatic ring.

With this in mind, methyl-substituted monoaromatics, preferably monoaromatics only substituted with methyls, can be directly exploited, which is not the case with monoaromatics containing no methyl (example: ethylbenzene, propylbenzene). It is therefore preferable to convert these monoaromatics into aromatics (e.g only) substituted with methyls. In this context, a device has been developed for converting alkyl aromatics comprising a hydrogenolysis unit capable of increasing the amount of methyl groups on the aromatic rings, in particular to increase the production of para-xylene. The objective of the hydrogenolysis unit is to produce methyl groups instead of alkyl groups having more than two carbon atoms.

Specifically, the object of the invention is to improve the performance of the hydrogenolysis unit. It has been observed that the catalysts used can cause a side demethylation reaction which is detrimental to the overall yield of the hydrogenolysis unit. It is proposed to add, upstream of the hydrogenolysis unit, an extraction (or depletion) unit in order to reduce the content of methyl-substituted compounds, and preferably of compounds only substituted with methyls (xylenes, trimethylbenzenes, tetramethylbenzenes, etc.). These compounds do not need to be converted before transalkylation and therefore do not need to be treated by the unit for hydrogenolysis of alkyl aromatics. Thus the feedstock of the hydrogenolysis unit is depleted in methyl groups which allows the hydrogenolysis unit to treat predominantly aromatics having at least one alkyl chain with 2 or more carbons. Thus losses by demethylation in the hydrogenolysis unit are reduced, resulting in a gain in the selectivity of the unit.

The present invention thus relates to a device and a process for converting aromatic compounds, making it possible to extract methyl-substituted aromatic compounds from a hydrocarbon feedstock rich in aromatic compounds having at least 8 carbon atoms in a unit for extracting aromatics, and thus to produce at least one effluent enriched in methyl-substituted aromatic compounds and an effluent depleted in methyl-substituted aromatic compounds; and making it possible to convert, into methyl groups, C2+ alkyl chains of the aromatic compounds of the depleted effluent in a hydrogenolysis unit placed downstream (e.g. directly downstream) of the unit for extracting aromatics, and thus to produce a hydrogenolysis effluent enriched in methyl-substituted aromatic compounds.

Figure 1:
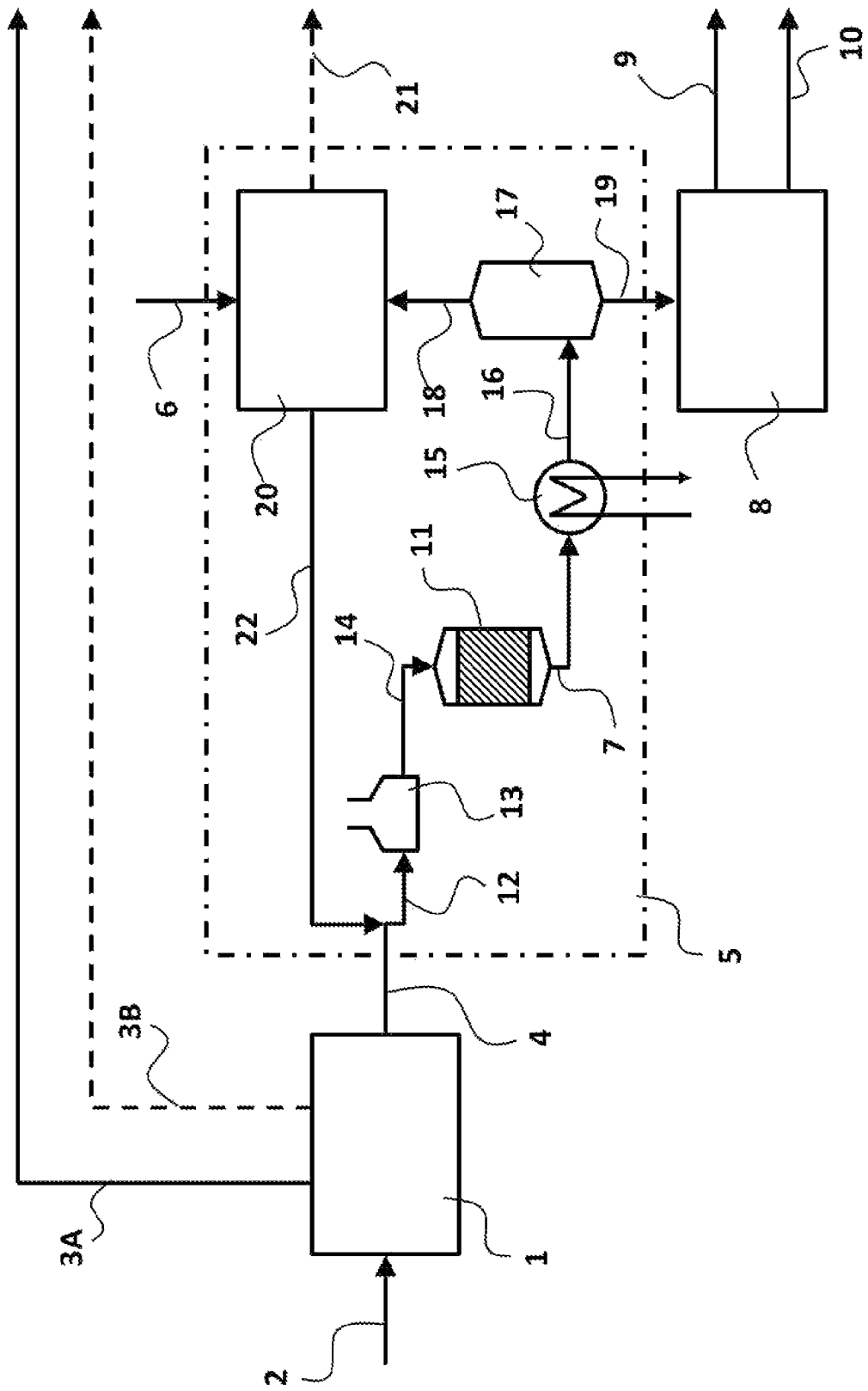
FIG. 1 represents a device for converting aromatic compounds according to one or more embodiments of the present invention, comprising a unit for extracting methyl-substituted aromatic compounds and a unit for the hydrogenolysis of the C2+ alkyl chains of the aromatic compounds.

Referring to FIG. 1, the conversion device comprises an extraction unit 1 suitable for:
- treating the hydrocarbon feedstock 2 in order to extract methyl-substituted aromatic compounds; and
- producing a first effluent enriched in methyl-substituted aromatic compounds 3A and the effluent depleted in methyl-substituted aromatic compounds 4.

According to one or more embodiments, the extraction unit 1 is suitable for extracting aromatic compounds mainly and preferably only substituted with methyls, and producing at least one effluent enriched in aromatic compounds only substituted with methyls and an effluent depleted in aromatic compounds only substituted with methyls.

According to one or more embodiments, the effluent enriched in methyl-substituted aromatic compounds 3A comprises at least 90% by weight, preferably at least 95% by weight, very preferably at least 99% by weight, of aromatic compounds only substituted with methyls (e.g. xylenes, trimethylbenzenes and/or tetramethylbenzenes) relative to the total weight of said effluent enriched in methyl-substituted aromatic compounds 3A.

According to one or more embodiments, the extraction unit 1 is suitable for producing at least a second effluent enriched in methyl-substituted aromatic compounds 3B. For example, the extraction unit 1 can be configured to extract a first enriched effluent 3A comprising xylenes; and to extract a second enriched effluent 3B comprising trimethylbenzenes. The extraction unit 1 can further be configured to extract a third effluent comprising, for example, tetramethylbenzenes.

According to one or more embodiments, the extraction unit 1 comprises at least one distillation column, and/or a molecular sieve simulated moving bed, and/or a molecular sieve adsorption unit which can be regenerated at temperature and/or under differential pressure, and/or a crystallization unit, and/or a liquid/liquid extraction unit, and/or an extractive distillation unit, and/or a membrane separation unit. For example, the extraction unit 1 can comprise one or more distillation columns suitable for separating xylenes and/or trimethylbenzenes and/or tetramethylbenzenes from the hydrocarbon feedstock 2. According to one or more embodiments, the extraction unit 1 comprises the raffinate column of a para-xylene extraction unit. According to one or more embodiments, the extraction unit comprises a simulated moving bed suitable for treating the raffinate from a para-xylene extraction unit and producing an effluent depleted in methyl-substituted aromatic compounds 4 comprising (e.g. essentially) ethylbenzene and at least one effluent enriched in methyl-substituted aromatic compounds (3A, 3B) comprising (e.g. essentially) meta-xylene and/or ortho-xylene.

According to one or more embodiments, the extraction unit 1 comprises at least one of the following distillation columns:
- column which recovers xylenes at the bottom of the column (e.g. distillation column of example 4),
- column which recovers methylethylbenzenes at the top of the column (e.g. distillation column C1 of example 2);
- column which recovers trimethylbenzenes at the top of the column (e.g. distillation column C2 of example 2).

According to one or more embodiments, the column which recovers xylenes at the bottom of the column is used with at least one of the following operating conditions:
- reflux drum: approximately 0.001-0.1 MPag and approximately 115-155° C.;
- column: approximately 40-100 theoretical plates, weight ratio of the reflux and feedstock flow rates approximately equal to 0.5-10, temperature at the top of the column: approximately 120-160° C., temperature at the bottom of the column: approximately 140-180° C.

According to one or more embodiments, the column which recovers xylenes at the bottom of the column is used with at least one of the following operating conditions:
- reflux drum: approximately 0.01 MPag and approximately 136° C.;
- column: approximately 70 theoretical plates, weight ratio of the reflux and feedstock flow rates approximately equal to 7.7, temperature at the top of the column: approximately 141° C., temperature at the bottom of the column: approximately 159° C.

According to one or more embodiments, the column which recovers methylethylbenzenes at the top of the column is used with at least one of the following operating conditions:
- reflux drum: approximately 0.001-0.1 MPag and approximately 140-180° C.;
- column: approximately 40-100 theoretical plates, weight ratio of the reflux and feedstock flow rates approximately equal to 0.5-10, temperature at the top of the column: approximately 150-190° C., temperature at the bottom of the column: approximately 180-220° C.

According to one or more embodiments, the column which recovers methylethylbenzenes at the top of the column is used with at least one of the following operating conditions:
- reflux drum: approximately 0.01 MPag and approximately 157° C.;
- column: approximately 72 theoretical plates, weight ratio of the reflux and feedstock flow rates approximately equal to 4.7, temperature at the top of the column: approximately 172° C., temperature at the bottom of the column: approximately 203° C.

According to one or more embodiments, the column which recovers trimethylbenzenes at the top of the column is used with at least one of the following operating conditions:
- reflux drum: approximately 0.001-0.1 MPag and approximately 150-190° C.;
- column: approximately 20-60 theoretical plates, weight ratio of the reflux and feedstock flow rates approximately equal to 0.5-10, temperature at the top of the column: approximately 160-200° C., temperature at the bottom of the column: approximately 180-220° C.

According to one or more embodiments, the column which recovers trimethylbenzenes at the top of the column is used with at least one of the following operating conditions:
- reflux drum: approximately 0.01 MPag and approximately 168° C.;
- column: approximately 36 theoretical plates, weight ratio of the reflux and feedstock flow rates approximately equal to 1.8, temperature at the top of the column: approximately 183° C., temperature at the bottom of the column: approximately 203° C.

According to one or more embodiments, the hydrocarbon feedstock 2 comprises at least 80% by weight of aromatics relative to the total weight of said hydrocarbon feedstock 2.

According to one or more embodiments, the hydrocarbon feedstock 2 comprises at least 80% by weight of aromatics comprising at least 8 carbon atoms relative to the total weight of said hydrocarbon feedstock 2. According to one or more embodiments, the hydrocarbon feedstock 2 comprises at least 90% by weight of aromatics comprising at least 8 carbon atoms relative to the total weight of said hydrocarbon feedstock 2.

According to one or more embodiments, the hydrocarbon feedstock 2 comprises at least 10% by weight, preferably at least 20% by weight, preferentially at least 40% by weight, of aromatic molecules comprising at least one C2+ alkyl (e.g. ethyl, propyl, butyl, etc.) chain relative to the total weight of the hydrocarbon feedstock 2.

According to one or more embodiments, the hydrocarbon feedstock 2 comprises at least 90% by weight of aromatic molecules having between 8 and 10 carbon atoms relative to the total weight of said hydrocarbon feedstock 2. According to one or more embodiments, the hydrocarbon feedstock comprises at least one internal stream of an aromatic complex for the production of para-xylene and/or the hydrogenolysis effluent is a feedstock sent to an aromatic complex for the production of para-xylene.

According to one or more embodiments, the hydrocarbon feedstock 2 comprises at least 90% by weight of aromatic molecules having 8 carbon atoms relative to the total weight of said hydrocarbon feedstock 2. According to one or more embodiments, the hydrocarbon feedstock 2 comprises a para-xylene extraction raffinate. According to one or more embodiments, the para-xylene extraction raffinate comprises (e.g. essentially) ortho-xylene, meta-xylene and ethylbenzene. According to one or more embodiments, the para-xylene extraction raffinate comprises (e.g. essentially) meta-xylene and ethylbenzene.

According to one or more embodiments, the hydrocarbon feedstock 2 comprises at least 90% by weight of aromatic molecules having 9 carbon atoms relative to the total weight of said hydrocarbon feedstock 2. According to one or more embodiments, the hydrocarbon feedstock 2 comprises methylethylbenzenes and optionally trimethylbenzenes, preferably little or no trimethylbenzenes.

According to one or more embodiments, the hydrocarbon feedstock 2 comprises at least 90% by weight of aromatic molecules having 10 carbon atoms relative to the total weight of said hydrocarbon feedstock 2. According to one or more embodiments, the hydrocarbon feedstock comprises tetramethylbenzenes and/or dimethylethylbenzenes and/or methylpropylbenzenes, preferably little or no tetramethylbenzenes.

According to one or more embodiments, the hydrocarbon feedstock 2 comprises at least 85% by weight (e.g. at least 90% by weight) of aromatic molecules having between 9 and 10 carbon atoms, and between 0 and 15% by weight (e.g. between 1% and 10% by weight) of aromatic molecules having (e.g. at least) 11 carbon atoms relative to the total weight of said hydrocarbon feedstock 2.

The conversion device further comprises a hydrogenolysis unit 5 suitable for:
  treating the effluent 4 depleted in methyl-substituted aromatic compounds, by means of a supply of hydrogen 6 and in the presence of a catalyst, in order to convert the C2+ alkyl chains of the aromatic compounds into methyl groups; and
  producing the hydrogenolysis effluent 7 enriched in methyl-substituted aromatic compounds.

According to one or more embodiments, the hydrogenolysis unit 5 is suitable for treating the depleted effluent 4 by converting one or more alkyl groups with at least two carbon atoms (ethyl, propyl, butyl, isopropyl, etc., groups) attached to a benzene ring into one or more methyl groups, i.e., groups formed of a single $CH_3$ group.

According to one or more embodiments, the hydrogenolysis unit 5 comprises at least one hydrogenolysis reactor 11 suitable for use under the following operating conditions:
  temperature of between 300° C. and 550° C., preferentially of between 350° C. and 500° C., and more preferentially still of between 370° C. and 450° C.; and/or
  pressure of between 0.1 and 3 MPa, preferentially of between 0.2 and 2 MPa, and more preferentially of between 0.2 and 1 MPa; and/or
  $H_2$/HC molar ratio of between 1 and 10, and preferentially of between 1.5 and 6; and/or
  WWH of between 0.1 and 50 $h^{-1}$ (e.g. 1-50 $h^{-1}$), preferentially of between 0.5 and 30 $h^{-1}$ (e.g. 2-30 $h^{-1}$), and more preferentially of between 1 and 20 $h^{-1}$ (e.g. 5-20 $h^{-1}$).

The term "WWH" corresponds to the hourly weight of hydrocarbon feedstock injected, based on the weight of catalyst charged.

According to one or more embodiments, the hydrogenolysis reactor 11 is of fixed bed type and the catalyst support is in the form of extrudates.

According to one or more embodiments, the hydrogenolysis reactor 11 is of moving bed type, and the catalyst support is in the form of approximately spherical beads. A moving bed may be defined as being a gravity flow bed, such as those encountered in the catalytic reforming of gasolines.

According to one or more embodiments, the hydrogenolysis reactor 11 is operated in the presence of a catalyst comprising at least one metal from group VIII of the Periodic Table, preferably nickel and/or cobalt, deposited on a porous support comprising at least one crystalline or noncrystalline refractory oxide having structured or unstructured porosity. According to one or more embodiments, the metal from group VIII is nickel. The presence of a promoter (group VIB, VIIB, VIII, IB, IIB) is also possible. The catalyst is supported on a refractory oxide (e.g., alumina or silica), which has optionally been neutralized by treatment with a base.

In the present specification, the groups of chemical elements are given, unless otherwise specified, according to the CAS classification (CRC Handbook of Chemistry and Physics, published by CRC Press, Editor in Chief D. R. Lide, 81st edition, 2000-2001). For example, group VIII according to the CAS classification corresponds to the metals from columns 8, 9 and 10 according to the new IUPAC classification; group VIb according to the CAS classification corresponds to the metals from column 6 according to the new IUPAC classification.

According to one or more embodiments, the content of group VIII metal is between 0.01% and 50% by weight of said element, preferably between 0.05% and 25% by weight of the mass of the catalyst and more preferentially between 0.5% and 15% by weight relative to the total weight of the catalyst.

According to one or more embodiments, the cobalt content in the catalyst is between 0.25% and 30% by weight, preferably between 0.5% and 20% by weight, even more preferably between 1% and 10% by weight, of the mass of the catalyst.

According to one or more embodiments, the nickel content in the catalyst is between 0.1% and 25% by weight, preferably between 0.2% and 15% by weight, even more preferably between 0.5% and 10% by weight, of the mass of the catalyst.

According to one or more embodiments, the catalyst further comprises at least one "selectivating" second metal (that limits the positions of adsorption of the aromatics on the metal particles). According to one or more embodiments, the second metal is chosen from the group consisting of Mo, Cu, Fe, Zn, Sn, W, Ti and Mn, Ag and Sn, Cr. According to one or more embodiments, the second metal is chosen from the group consisting of Mo and Fe.

According to one or more embodiments, the atomic ratio between the "selectivating" second metal and the group VIII metal is between 0.1 and 2, preferably between 0.1 and 1.5, even more preferably between 0.2 and 1.2. It is understood that the atomic ratio between the selectivating metal and the group VIII metal is chosen so that the metal contents described above are observed.

According to one or more embodiments, the catalyst comprises nickel and molybdenum; the molybdenum content is between 0.1% and 20% by weight of said element relative to the total weight of the catalyst, preferably between 0.2% and 18% by weight, preferably between 0.4% and 15% by weight relative to the total weight of the catalyst; the catalyst comprises a molybdenum to nickel (Mo/Ni) molar ratio of between 0.2 and 0.9 (mol/mol), preferably between 0.4 and 0.9, and even more preferentially between 0.5 and 0.9.

According to one or more embodiments, the catalyst comprises nickel and iron; the iron content is between 0.1% and 20% by weight of said element relative to the total weight of the catalyst, preferably between 0.2% and 15% by weight, preferably between 0.4% and 13% by weight relative to the total weight of the catalyst; the catalyst comprises an iron to nickel (Fe/Ni) molar ratio of between 0.75 and 1.2 (mol/mol), preferably between 0.8 and 1.2, and even more preferentially between 0.9 and 1.2.

According to one or more embodiments, the refractory oxide may or may not be crystalline, and may or may not have a structured porosity. According to one or more embodiments, the refractory oxide is selected from the oxides of metals from groups 2, 3, 4, 13 and 14 of the IUPAC new periodic table of the elements, such as, for example, the oxides of magnesium, aluminum, silicon, titanium, zirconium, thorium, taken alone or as a mixture with each other, or as a mixture with other oxides of metals of the periodic table. According to one or more embodiments, the refractory oxide is inorganic. According to one or more embodiments, the refractory oxide is essentially neutral in terms of acidity-basicity. According to one or more embodiments, the refractory oxide is chosen from silicas of low surface area (i.e. BET<250 m$^2$/g; e.g. with less than 100 ppm by weight of Al), titanium oxides, aluminas (e.g. with less than 100 ppm by weight of Si), clays and charcoals. According to one or more embodiments, the refractory oxide is heat pretreated, optionally in the presence of water. According to one or more embodiments, the porous support is chosen from the group consisting of silica and alumina. According to one or more embodiments, the support is alumina.

According to one or more embodiments, the refractory oxide is hydrothermally pretreated, for example to adjust its surface area (in the sense of the BET surface area) downward and its pore distributions upward.

According to one or more embodiments, the (BET) specific surface area of the refractory oxide is generally greater than 1 m$^2$/g and less than 250 m$^2$/g, for example between 2 and 200 m$^2$/g, preferably between 5 and 100 m$^2$/g, preferentially less than 100 m$^2$/g, and even more preferentially between 20 and 90 m$^2$/g, such as approximately 80 m$^2$/g.

According to one or more embodiments, the pore volume (Vp) of the refractory oxide is between 0.1 and 2 cm$^3$/g, preferably between 0.3 and 1.5 cm$^3$/g, and even more preferentially between 0.9 and 1.1 cm$^3$/g, such as approximately 1.0 cm$^3$/g.

The refractory oxide can also include impurities (e.g. Ca, K, P, Mg, Fe, Si, Ti, W). According to one or more embodiments, the refractory oxide comprises less than 500 ppm by weight of impurities, preferably less than 200 ppm by weight of impurities, and even more preferentially less than 100 ppm by weight of impurities relative to the total weight of the refractory oxide.

The catalyst can also comprise at least one basic compound in order to limit reactions of an acidic nature (dealkylation of isopropylbenzene for example). According to one or more embodiments, the at least one basic compound is chosen from the group consisting of Na, K, Li and Ca. According to one or more embodiments, the content of basic compound is between 1% and 3% by weight, preferably between 1% and 2% by weight, of said basic compound relative to the total weight of the catalyst.

Said catalyst is generally presented in all the forms known to those skilled in the art, for example in the form of beads (generally having a diameter of between 1 and 8 mm), of extrudates, of blocks or of hollow cylinders. According to one or more embodiments, the catalyst consists of extrudates with a mean diameter generally of between 0.5 and 10 mm, preferably between 0.8 and 3.2 mm and very preferably between 1.0 and 2.5 mm and optionally with a mean length of between 0.5 and 20 mm. The term "mean diameter" of the extrudates is intended to mean the mean diameter of the circle circumscribing the cross section of these extrudates. The catalyst can advantageously be presented in the form of cylindrical, multilobal, trilobal or quadrilobal extrudates. Preferably, its shape will be trilobal or quadrilobal. The shape of the lobes could be adjusted according to all the methods known from the prior art.

According to one or more embodiments, the depleted effluent 4 is mixed with the hydrogen supply 6 in the hydrogenolysis reactor 11 and/or (e.g. directly) upstream of the hydrogenolysis reactor 11 to form a depleted effluent mixture 12.

According to one or more embodiments, the hydrogenolysis unit 5 further comprises a heating unit 13 for heating the depleted effluent 4 or the depleted effluent mixture 12 (e.g. directly) upstream of the hydrogenolysis reactor 11. The heating unit 13 may be preceded by equipment for recovering heat from the effluent 7 used to preheat the depleted effluent 4 or the depleted mixture 12. According to one or more embodiments, the heating unit 13 is suitable for use under the following operating conditions: inlet temperature of between 25° C. and 400° C.; and/or outlet temperature of between 100° C. and 550° C. The heating effluent 14 from the heating unit 13 is sent (e.g. directly) to the hydrogenolysis reactor 11.

According to one or more embodiments, the hydrogenolysis effluent 7 is sent (e.g. directly) to a cooling unit 15 (e.g. heat exchanger) to form a cooled hydrogenolysis effluent 16. The cooling unit 15 may be preceded by equipment for recovering heat from the effluent 7 used to preheat the depleted effluent 4 or the depleted mixture 12. According to one or more embodiments, the cooling unit 15 is suitable for use under the following operating conditions: inlet temperature of between 100° C. and 550° C.; and/or outlet temperature of between 25° C. and 400° C.

According to one or more embodiments, the cooled hydrogenolysis effluent 16 is sent (e.g. directly) to a cooled effluent separation unit 17 to produce a gaseous effluent 18 comprising hydrogen and a liquid effluent 19.

According to one or more embodiments, the gaseous effluent 18 is sent to a recycling unit 20 suitable for: compressing and/or purifying the gaseous effluent 18; optionally extracting a purge gas 21 (e.g. methane) from the gaseous effluent 18; and/or mixing the gaseous effluent 18 with the hydrogen supply 6 to form a hydrogen mixture 22 sent to the hydrogenolysis reactor 11 and/or (e.g. directly) mixed with the depleted effluent 4 to form the depleted effluent mixture 12.

According to one or more embodiments, a hydrogenolysis effluent separation unit 8 is placed (e.g. directly) downstream of the hydrogenolysis unit 5, to treat the hydrogenolysis effluent 7 (e.g. treatment of the liquid effluent 19 leaving the cooled effluent separation unit 17) and to produce a plurality of liquid effluent cuts 9 and 10.

According to one or more embodiments, the conversion device is integrated into an aromatic complex, for example in a device and/or process for producing xylenes using an aromatic complex. The conversion device then exchanges streams with the aromatic complex. According to one or more embodiments, the aromatic complex is fed with hydrocarbon cuts containing predominantly molecules, the carbon number of which extends from 6 to 10.

According to one or more embodiments, the following configurations of a conversion device integrated into an aromatic complex are envisioned.

The conversion device is used as a pretreatment unit upstream of the aromatic complex. In this case, external streams can directly feed the conversion device (example 6 to 10 carbon reformate, A9/A10 cut, etc.), and the effluents from the conversion device are then sent to the aromatic complex.

One or more conversion devices is/are used to treat one or more cuts internal to the aromatic complex. In this case, the conversion device can be partially or totally fed with one or more streams coming from units (e.g. fractionation/distillation columns, simulated moving bed) of the aromatic complex. The effluents from the conversion device are then also returned to the aromatic complex.

The combination of the two configurations defined above is also possible and remains within the context of the present invention. In all cases, the effluents are then enriched in aromatics comprising methyl groups, all or a portion of which are sent to the aromatic complex in order to produce xylenes and benzene. Overall, as will be shown in the example of FIG. 2 described below, the integration of the conversion device into the aromatic complex increases the production of para-xylene.

According to one or more embodiments, the conversion device is suitable for treating a stream containing aromatics with 8 and/or 9 and/or 10 carbon atoms internal to the aromatic complex. For example, FIG. 2 shows a conversion device 100 integrated into an aromatic complex in order to treat a stream containing aromatics with 9 and 10 carbon atoms resulting from the fractionating train of the aromatic complex.

Figure 2:
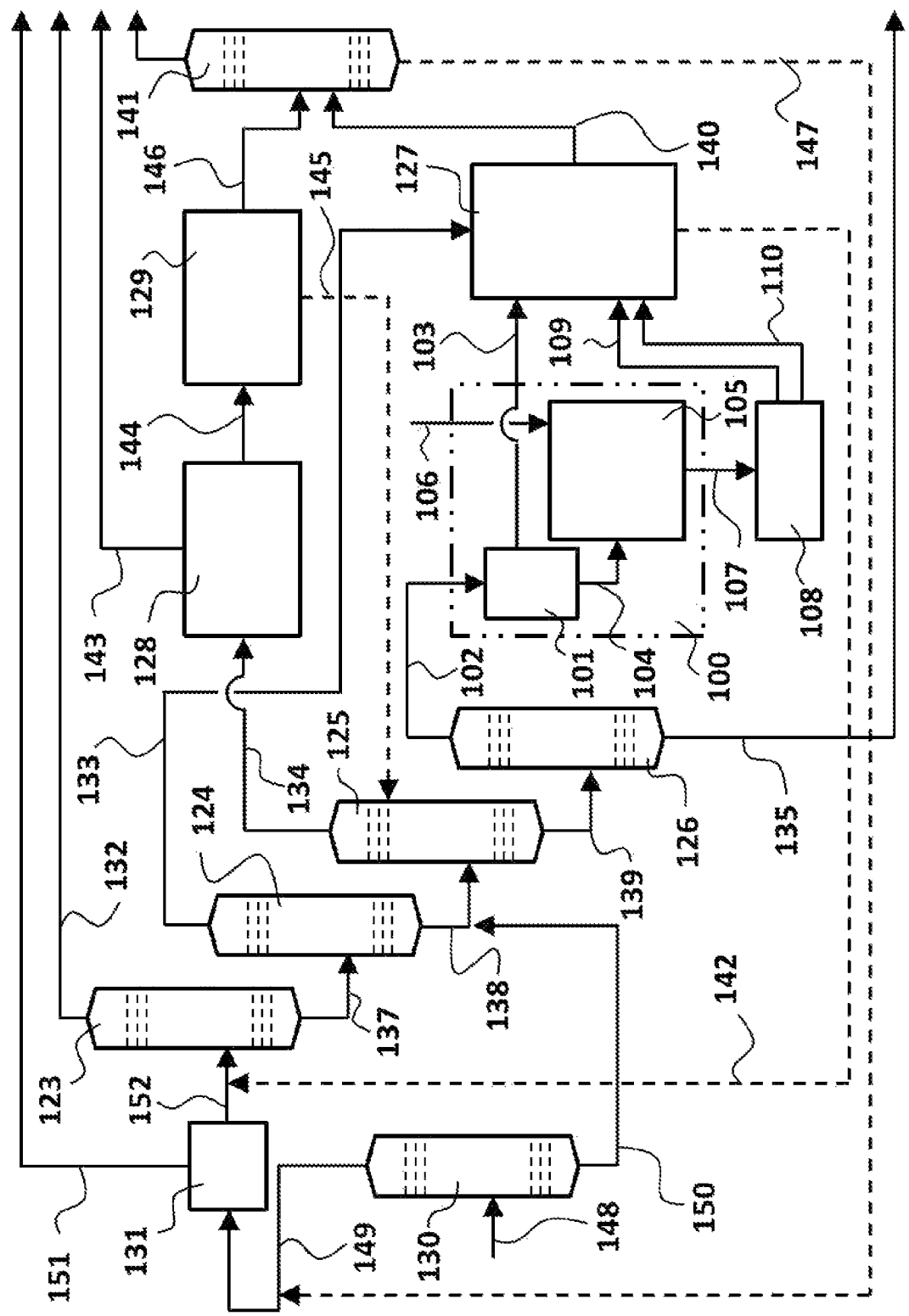
FIG. 2 represents an aromatic complex for the production of para-xylene comprising a device for converting aromatic compounds according to one or more embodiments of the present invention suitable for producing effluents enriched in methyl-substituted aromatic compounds from a C9-C10 feedstock.

Referring to FIG. 2, according to one or more embodiments, the aromatic complex comprises:

the conversion device 100, in which: the extraction unit 101 is suitable for treating the aromatics having between 9 and 10 carbon atoms 102, which are imported or extracted from internal streams of the aromatic complex, and providing an effluent 103 enriched in aromatic compounds (e.g. only) substituted with methyls and an effluent 104 depleted in aromatic compounds (e.g. only) substituted with methyls, and in which the selective hydrogenolysis unit 105 is suitable for treating the depleted effluent 104 with a hydrogen supply 106 and producing the hydrogenolysis effluent enriched in methyl-substituted aromatic compounds 107;

an optional hydrogenolysis effluent separation unit 108 placed (e.g. directly) downstream of the selective hydrogenolysis unit 105, in order to produce a plurality of liquid effluent cuts 109 and 110;

a fractionating train 123-126 that makes it possible to extract the xylenes from the other aromatics;

a transalkylation unit 127 that converts toluene and methylalkylbenzenes such as trimethylbenzenes into xylenes; advantageously, this unit can also treat tetramethylbenzenes and, to a certain extent, benzene;

a xylene separation unit 128 (e.g. of simulated moving bed type using a molecular sieve and a desorbent) that enables the para-xylene to be isolated from the xylenes and ethylbenzene;

an optional unit 129 for isomerizing the raffinate obtained as effluent from the xylene separation unit 128, in order to convert in particular ortho-xylene, meta-xylene and ethylbenzene into para-xylene;

an optional feedstock separation unit 130 upstream of the fractionating train 123-126 in order to separate a hydrocarbon cut having 7 carbon atoms or fewer (C7−) and an aromatic cut having 8 carbon atoms or more (A8+) from the feedstock of the aromatic complex;

an optional aromatics extraction unit 131 between the feedstock separation unit 130 and the fractionating train 123-126 in order to separate the aliphatic compounds from the benzene and the toluene of the C7− cut of the feedstock of the complex.

According to one or more embodiments, the fractionating train comprises the columns 123, 124, 125 and 126 for distilling aromatic compounds, enabling the following 5 cuts to be separated:

a cut 132 comprising (e.g., essentially) aromatic compounds having 6 carbon atoms (e.g. benzene);

a cut 133 comprising (e.g., essentially) aromatic compounds having 7 carbon atoms (e.g. toluene);

a cut 134 comprising (e.g., essentially) aromatic compounds having 8 carbon atoms (e.g. xylenes and ethylbenzene);

a cut 102 comprising (e.g., essentially) aromatic compounds having 9 and 10 carbon atoms; and a cut 135 comprising (e.g., essentially) aromatic compounds, of which the most volatile species are aromatics having 10 carbon atoms.

The column 123 for distilling aromatic compounds, also referred to as benzene column, is suitable for: treating a C6-C10 (e.g., essentially) aromatic (A6+) hydrocarbon feedstock 136; producing at the top the cut 132 (benzene cut) which is one of the desired products exiting the aromatic complex; and producing at the bottom a C7-C10 (e.g., essentially) aromatic (A7+) effluent 137. According to one or more embodiments, the C6-C10 (e.g., essentially) aromatic (A6+) hydrocarbon feedstock 136 is a the C6-C7 (e.g. essentially) aromatic (A6-A7) hydrocarbon feedstock.

The column 124 for distilling aromatic compounds, also referred to as toluene column, is suitable for: treating the (A7+) effluent 137 from the bottom of the benzene column; producing at the top the cut 133 (toluene cut) which is sent to the transalkylation unit 127; and producing at the bottom a C8-C10 (e.g., essentially) aromatic (A8+) effluent 138.

The column 125 for distilling aromatic compounds, also referred to as xylene column, is suitable for: treating the effluent 138 from the bottom of the toluene column and optionally an aromatic cut having 8 carbon atoms or more (A8+) of the feedstock of the aromatic complex; producing at the top the cut 134 (xylene and ethylbenzene cut) which is sent to the xylene separation unit 128; and producing at the bottom a C9-C10 (e.g., essentially) aromatic (A9+) effluent 139.

The column 126 for distilling aromatic compounds, also referred to as heavy aromatics column, is suitable for: treating the effluent 139 from the bottom of the xylene column; producing at the top the hydrocarbon feedstock 102 of the conversion device 100 which is sent to the extraction unit 101, the hydrocarbon feedstock 102 comprising (e.g., essentially) C9-C10 monoaromatics; and producing at the bottom the cut comprising (e.g. essentially) aromatic compounds of which the most volatile species are aromatics having 10 carbon atoms (A10+) 135.

With reference to FIG. 2, the hydrogenolysis effluent enriched in methyl-substituted aromatic compounds 107 from the selective hydrogenolysis unit 105 is sent to the optional hydrogenolysis effluent separation unit 108 in order to produce a plurality of liquid effluent cuts, including a light fraction 109 comprising (e.g. essentially) hydrocarbon compounds with 8 carbon atoms or fewer (C8−) and a heavy fraction 110 (e.g. essentially) of aromatic compounds with 9 carbon atoms or more (A9+).

According to one or more embodiments, the light fraction 109 is sent (directly) to the fractionating train 123-126 and the heavy fraction 110 is sent to the transalkylation unit 127. According to one or more embodiments, the light fraction 109 and the heavy fraction 110 are sent to the transalkylation unit 127. According to one or more embodiments, the light fraction 109 short-circuits the reaction section (not shown) of the transalkylation unit 127 in order to feed a first separation column (not shown) downstream of said reaction section of the transalkylation unit 127.

In the transalkylation unit 127, the heavy fraction 110 is mixed with the a cut 133 comprising (e.g. essentially) aromatic compounds having 7 carbon atoms (e.g. toluene) originating from the top of the toluene column 124, and feeds the reaction section of the transalkylation unit 127 in order to produce xylenes by transalkylation of aromatics with a deficit of methyl groups (toluene) and aromatics with an excess of methyl groups (e.g., tri- and tetramethylbenzenes).

According to one or more embodiments, the effluents from the reaction section of the transalkylation unit 127 are separated in the first separation column. A cut 140 comprising at least a portion of the benzene, and the more volatile (C6−) species is extracted at the top of the first separation column and is sent to an optional stabilization column 141. The heavy fraction 142 of the effluents from the first separation column, comprising (e.g., essentially) aromatics having at least 7 carbon atoms (A7+), is optionally recycled to the fractionating train 123-126, for example to the benzene column 123.

The cut 134 comprising (e.g., essentially) aromatic compounds having 8 carbon atoms (e.g. xylenes and ethylbenzene) is treated in the xylene separation unit 128. The para-xylene 143 is exported as main product. The raffinate 144 from the xylene separation unit 128 comprising (e.g. essentially) ortho-xylene, meta-xylene and ethylbenzene feeds the isomerization unit 129.

In the isomerization reaction section (not shown) of the isomerization unit 129, isomers of para-xylene are isomerized while ethylbenzene is dealkylated to produce benzene. According to one or more embodiments, the effluents from the isomerization reaction section are sent to a second separation column (not shown) to produce, at the bottom, a para-xylene-enriched isomerate 145, which is optionally recycled to the xylene column 125; and to produce, at the top, a hydrocarbon cut 146 comprising compounds having 7 carbon atoms or fewer (C7−), which is sent to the stabilization column 141, for example with the cut 140 comprising at least a portion of the benzene, and the more volatile species.

According to one or more embodiments, the stabilization column 141 produces, at the bottom, a stabilized cut 147 comprising (e.g. essentially) benzene and toluene, which is optionally recycled to the inlet of the aromatics extraction unit 131.

According to one or more embodiments, the feedstock separation unit 130 treats the incoming feedstock 148 of the aromatic complex, to separate an overhead cut 149 comprising (e.g. essentially) compounds having 7 carbon atoms or fewer (C7−), and a bottom cut 150 comprising (e.g. essentially) aromatics having 8 carbon atoms or more (A8+), which is sent to the xylene column 125.

According to one or more embodiments, the incoming feedstock 148 is a hydrocarbon cut containing predominantly molecules of which the carbon number extends from 6 to 10 carbon atoms. This feedstock may also contain molecules having more than 10 carbon atoms and/or molecules having 5 carbon atoms. The incoming feedstock 148 of the aromatic complex is rich in aromatics and contains at least 50% by weight of alkyl aromatics, preferentially more than 70%, the incoming feedstock 148 can be produced by catalytic reforming of a naphtha or be a product of a cracking unit (e.g. steam or catalytic cracking unit) or any other means of producing alkyl aromatics.

The overhead cut 149 from the feedstock separation unit 130, optionally mixed with the bottom product (benzene and toluene) from the stabilization column (141), is sent to the aromatics extraction unit 131 in order to extract an effluent 151 comprising C6-C7 aliphatic species, which is exported as a co-product of the aromatic complex. The aromatic cut 152 (essentially benzene and toluene) referred to as the extract from the aromatics extraction unit 131, optionally mixed with the heavy cut 142, is sent to the column 123 for distilling aromatic compounds.

Example from FIG. 2 described above relates to an embodiment in which the conversion device is suitable for treating a stream containing aromatics with 9 and 10 carbon atoms resulting from the fractionating train of the aromatic complex. It should be noted that other configurations, alone or in combinations, are also envisioned. As described in example 4 below, a conversion device according to the present description can also be provided to treat a stream containing aromatics with 8 carbon atoms resulting from the raffinate (effluent comprising (e.g. essentially) ortho-xylene and/or meta-xylene and/or ethylbenzene) obtained as effluent from the xylene separation unit of the aromatic complex. It is a question, for example, of separating, in the extraction unit 1, an effluent comprising (e.g. essentially) ethylbenzene from at least one effluent comprising methylated aromatics and of hydrogenolysing the ethylbenzene in the hydrogenolysis unit 5 in order to produce toluene which will be reintroduced into the aromatic complex, for example into the transalkylation unit.

EXAMPLES

Example 1

The selective hydrogenolysis unit of a reference conversion device is supplied with a feedstock throughput of 100 t/h containing C9 aromatics, the composition of which in % by weight is defined in table 1 below.

TABLE 1

| ETHYLBENZENE | 0.1% |
| --- | --- |
| PARA-XYLENE | 0.0% |
| META-XYLENE | 0.5% |
| ORTHO-XYLENE | 0.9% |
| ISOPROPYLBENZENE | 0.4% |
| N-PROPYLBENZENE | 4.4% |
| 1-METHYL-2-ETHYLBENZENE | 10.2% |
| 1-METHYL-3-ETHYLBENZENE | 18.5% |
| 1-METHYL-4-ETHYLBENZENE | 8.6% |
| 1,2,3-TRIMETHYLBENZENE | 4.8% |
| 1,2,4-TRIMETHYLBENZENE | 39.8% |
| 1,3,5-TRIMETHYLBENZENE | 11.2% |
| INDANE | 0.7% |

The catalyst comprises 10% by weight of Ni and 7% by weight of Mo on alumina of 80 m$^2$/g, 1 cc/g of pore volume. The catalyst is in the form of a trilobe extrudate having an external diameter of 1.6 mm (3 to 6 mm long).

The catalyst is prepared by dry impregnation of the metal salts (nitrates or carbonates in the case herein), diluted in a solvent that can be vaporized in the heat treatment steps (for example, in the case herein, water or an aqueous solution of ammonia).

The operating conditions of the selective hydrogenolysis step are as follows:

H$_2$/HC (hydrocarbons) molar ratio: 3 mol/mol
pressure: 0.5 MPa
temperature: 390° C.
WWH=12 h$^{-1}$.

The WWH can be adapted to convert at least 40% (by weight or mol %) of the alkyl aromatics containing 2 or more carbon atoms. For example, the WWH can be chosen between 1 and 50 h$^{-1}$, preferentially between 2 and 30 h$^{-1}$ and more preferentially between 5 and 20 h$^{-1}$ (for example for a catalyst based on NiMo on alumina with an Mo/Ni weight ratio of 0.5).

Under these conditions, the performance of the unit is that presented in table 3 described below.

Example 2

Upstream of the selective hydrogenolysis unit 5, an extraction unit 1 is arranged to deplete the feedstock in trimethylbenzenes. The extraction is carried out by the linking in series of two distillation columns C1 and C2:
- a first distillation column C1 for: treating the hydrocarbon feedstock 2; and recovering a column overhead effluent comprising methylethylbenzenes and a bottom effluent comprising the other compounds; and
- a second distillation column C2 for: treating the bottom effluent from the first distillation column C1; and recovering a column overhead effluent comprising trimethylbenzenes (example of the enriched effluent 3A in FIG. 1) and a column bottom effluent comprising the other compounds.

In this example, the extraction consists in having a stream at the top of column C2 rich in trimethylbenzenes (example of the enriched effluent 3A in FIG. 1). In this example, the stream rich in methylethylbenzenes (top of column C1) is added to the bottom of column C2 to form the depleted effluent 4 feeding the selective hydrogenolysis unit 5. The composition in % by weight of said mixture is defined in table 2 below. It can also be envisioned not to use column C2 and to send only the top of column C1 mainly composed of methylethylbenzene.

The composition is obtained by treating the feedstock, the composition of which is presented in table 1.

TABLE 2

| ETHYLBENZENE | 0.2% |
| --- | --- |
| PARA-XYLENE | 0.0% |
| META-XYLENE | 1.0% |
| ORTHO-XYLENE | 1.8% |
| ISOPROPYLBENZENE | 0.8% |
| N-PROPYLBENZENE | 8.4% |
| 1-METHYL-2-ETHYLBENZENE | 19.4% |
| 1-METHYL-3-ETHYLBENZENE | 36.4% |
| 1-METHYL-4-ETHYLBENZENE | 10.5% |
| 1,2,3-TRIMETHYLBENZENE | 3.9% |
| 1,2,4-TRIMETHYLBENZENE | 7.3% |
| 1,3,5-TRIMETHYLBENZENE | 9.7% |
| INDANE | 0.7% |

The selective hydrogenolysis unit operates under the same conditions as the reference case (example 1) with the same catalyst. The comparison from table 3 between example 2 (subject of the invention) and example 1 (reference) confirms the advantage of the invention with a 6% increase in the amount of methyls available in the liquid products at the unit outlet (combination of streams 3B and 19).

TABLE 3

| | | Example 1 | Example 2 |
| --- | --- | --- | --- |
| Feedstock before extraction (hydrogenolysis inlet for example 1, extraction inlet for example 2) | | | |
| Amount of methyl | [kmol/h] | 1740 | 1740 |
| Amount of ring | [kmol/h] | 834 | 834 |
| methyl/ring ratio | [mol/mol] | 2.09 | 2.09 |
| Unit outlet | | | |
| Amount of methyl | [kmol/h] | 1685 | 1785 |
| Amount of ring | [kmol/h] | 814 | 813 |
| methyl/ring ratio | [mol/mol] | 2.07 | 2.20 |
| Methyl out/methyl in ratio | [mol/mol] | 0.97 | 1.03 |

Example 3

The selective hydrogenolysis unit of a reference conversion device is supplied with a feedstock throughput of 100 t/h containing C8 aromatics, the composition of which in % by weight is defined in table 4 below.

TABLE 4

| ETHYLBENZENE | 14.3% |
| --- | --- |
| PARA-XYLENE | 0.0% |
| META-XYLENE | 57.1% |
| ORTHO-XYLENE | 28.6% |

This is the raffinate from an extraction of para-xylene by SMB.

The selective hydrogenolysis unit, the catalyst and the operating conditions are identical to the case described in detail in example 1. The performance of the unit is presented in table 6 described below.

Example 4

This example illustrates the case of extraction of methyl-substituted aromatics from a feedstock of aromatics with 8 carbon atoms.

Upstream of the selective hydrogenolysis unit 5, an extraction unit 1 is arranged to deplete the feedstock in xylenes. The extraction is carried out by a distillation column, the overhead product of which is depleted in xylenes (example of depleted effluent 4 in FIG. 1) and feeds the selective hydrogenolysis unit 5.

The composition in % by weight of the xylene-depleted overhead product is defined in table 5 below. The composition is obtained by treating the feedstock, the composition of which is presented in table 4.

TABLE 5

| ETHYLBENZENE | 53.8% |
|---|---|
| PARA-XYLENE | 0.0% |
| META-XYLENE | 46.1% |
| ORTHO-XYLENE | 0.1% |

The selective hydrogenolysis unit operates under the same conditions as the reference case (example 3) with the same catalyst. The comparison from table 6 between example 4 (subject of the invention) and example 3 (reference) confirms the advantage of the invention with a 7% increase in the amount of methyls available in the liquid products at the unit outlet (combination of streams 3A and 19).

TABLE 6

| | | Example 3 | Example 4 |
|---|---|---|---|
| Feedstock before extraction (hydrogenolysis inlet for example 3, extraction inlet for example 4) | | | |
| Amount of methyl | [kmol/h] | 1615 | 1615 |
| Amount of ring | [kmol/h] | 942 | 942 |
| methyl/ring ratio | [mol/mol] | 1.71 | 1.71 |
| Unit outlet | | | |
| Amount of methyl | [kmol/h] | 1520 | 1630 |
| Amount of ring | [kmol/h] | 912 | 907 |
| methyl/ring ratio | [mol/mol] | 1.67 | 1.80 |
| Methyl out/methyl in ratio | [mol/mol] | 0.94 | 1.01 |

In the present specification, the term "comprise" is synonymous with (signifies the same thing as) "include" and "contain", and is inclusive or open, and does not exclude other elements which are not stated. It is understood that the term "comprise" includes the exclusive and closed term "consist". In addition, in the present description, the terms "approximately", "substantially", "more or less", "essentially", "solely" and "about" are synonymous with (mean the same thing as) margin lower and/or greater by 10%, preferably by 5%, very preferably by 1%, of the given value. For example, an effluent comprising essentially or solely compounds A corresponds to an effluent comprising at least 90%, preferably at least 95%, very preferably at least 99%, of compounds A.

The invention claimed is:

1. A device for converting aromatic compounds, comprising:
   an extraction unit (1) suitable for extracting methyl-substituted aromatic compounds from a hydrocarbon feedstock (2) comprising at least 85% by weight of aromatic molecules having between 9 and 10 carbon atoms, and between 0 and 15% by weight of aromatic molecules having 11 carbon atoms relative to the total weight of said hydrocarbon feedstock (2), and producing at least one effluent enriched in methyl-substituted aromatic compounds (3A, 3B) and one effluent depleted in methyl-substituted aromatic compounds (4); and
   a hydrogenolysis unit (5) placed downstream of the extraction unit (1) and suitable for converting, into methyl groups, C2+ alkyl chains of aromatic compounds of the effluent depleted in methyl-substituted aromatic compounds (4), and producing a hydrogenolysis effluent enriched in methyl-substituted aromatic compounds (7).

2. The conversion device as claimed in claim 1, wherein the extraction unit (1) is suitable for producing at least one effluent enriched in methyl-substituted aromatic compounds (3A, 3B) comprising at least 90% by weight of aromatic compounds only substituted with methyls relative to the total weight of said effluent enriched in methyl-substituted aromatic compounds (3A, 3B).

3. The conversion device as claimed in claim 1, wherein the extraction unit (1) comprises at least one of the following distillation columns:
   distillation column suitable for recovering xylenes at the bottom of the column;
   distillation column suitable for recovering the methylethylbenzenes at the top of the column;
   distillation column suitable for recovering the trimethylbenzenes at the top of the column.

4. The conversion device as claimed in claim 1, wherein the extraction unit (1) is suitable for producing at least a second effluent enriched in methyl-substituted aromatic compounds (3B).

5. The conversion device as claimed in claim 1, wherein the extraction unit (1) is suitable for:
   producing at least one effluent depleted in methyl-substituted aromatic compounds (4) comprising methylethylbenzenes and/or propylbenzenes and at least one effluent enriched in methyl-substituted aromatic compounds (3A, 3B) comprising trimethylbenzenes.

6. A device for producing xylenes integrating the device for converting aromatic compounds as claimed in claim 1, in order to enrich streams in aromatics comprising methyl groups, all or a portion of which are sent to an aromatic complex in order to produce xylenes.

7. The device for producing xylenes as claimed in claim 6, wherein at least one device for converting aromatic compounds is integrated into an aromatic complex according to at least one of the following configurations:
   the at least one device for converting aromatic compounds is used to pretreat the hydrocarbon feedstock (2) upstream of the aromatic complex;
   the at least one device for converting aromatic compounds is used to treat at least one cut internal to the aromatic complex.

8. A process for converting aromatic compounds, comprising the following steps:
   extracting methyl-substituted aromatic compounds from a hydrocarbon feedstock (2) comprising at least 85% by weight of aromatic molecules having between 9 and 10 carbon atoms, and between 0 and 15% by weight of aromatic molecules having 11 carbon atoms relative to the total weight of said hydrocarbon feedstock (2) in an extraction unit (1), in order to produce at least one effluent enriched in methyl-substituted aromatic compounds (3A, 3B) and one effluent depleted in methyl-substituted aromatic compounds (4); and converting, into methyl groups, C2+ alkyl chains of the aromatic compounds of the effluent depleted in methyl-substituted aromatic compounds (4) in a hydrogenolysis unit (5) placed downstream of the extraction unit (1), in order to produce a hydrogenolysis effluent enriched in methyl-substituted aromatic compounds (7).

9. The conversion process as claimed in claim 8, wherein at least one effluent enriched in methyl-substituted aromatic compounds (3A, 3B) is produced, comprising at least 90% by weight of aromatic compounds only substituted with methyls relative to the total weight of said effluent enriched in methyl-substituted aromatic compounds (3A, 3B).

10. The conversion process as claimed in claim 8, wherein at least one of the following compounds is extracted:
xylenes recovered at the bottom of a distillation column,
methylethylbenzenes recovered at the bottom of a distillation column,
trimethylbenzenes recovered at the bottom of a distillation column.

11. The conversion process as claimed in claim 8, wherein at least a second effluent enriched in methyl-substituted aromatic compounds (3B) is produced.

12. The conversion process as claimed in claim 8, wherein:
at least one effluent depleted in methyl-substituted aromatic compounds (4) comprising methylethylbenzenes and/or propylbenzenes and at least one effluent enriched in methyl-substituted aromatic compounds (3A, 3B) comprising trimethylbenzenes are produced.

13. The conversion process as claimed in claim 8, wherein the hydrogenolysis unit (5) is used with the following operating conditions:

temperature of between 300° C. and 550° C.;
pressure of between 0.1 and 3 MPa;
$H_2$/HC molar ratio of between 1 and 10;
WWH of between 0.1 and 50 $h^{-1}$.

14. A process for producing xylenes integrating the process for converting aromatic compounds as claimed in claim 8, in order to enrich streams in aromatics comprising methyl groups, all or a portion of which are sent to an aromatic complex in order to produce xylenes.

15. The process for producing xylenes as claimed in claim 14, wherein the process of converting aromatic compounds is integrated into an aromatic complex according to at least one of the following configurations:
pretreatment of the hydrocarbon feedstock (2) upstream of the aromatic complex;
treatment of at least one cut internal to the aromatic complex.

16. The conversion process as claimed in claim 10, wherein xylenes are recovered at the bottom of a distillation column, and the distillation column is operated at under the following conditions:
40-100 theoretical plates,
weight ratio of reflux and feedstock flow rates of 0.5-10,
temperature at the top of the column: 120-160° C., and
temperature at the bottom of the column: 140-180° C.

17. The conversion process as claimed in claim 10, wherein methylethylbenzenes are recovered at the bottom of a distillation column, and the distillation column is operated at under the following conditions:
40-100 theoretical plates,
weight ratio of reflux and feedstock flow rates of 0.5-10,
temperature at the top of the column: 120-160° C., and
temperature at the bottom of the column: 140-180° C.

18. The conversion process as claimed in claim 10, wherein trimethylbenzenes are recovered at the bottom of a distillation column, and the distillation column is operated at under the following conditions:
20-60 theoretical plates,
weight ratio of reflux and feedstock flow rates of 0.5-10,
temperature at the top of the column: 160-200° C., and
temperature at the bottom of the column: 180-220° C.

* * * * *